United States Patent [19]

Albers, Sr.

[11] 4,169,048
[45] Sep. 25, 1979

[54] ANAEROBIC FERMENTATION OF EXCRETA IN A COLLAPSIBLE BAG

[76] Inventor: Teo Albers, Sr., 18007 Arline Ave., Artesia, Calif. 90701

[21] Appl. No.: 934,857

[22] Filed: Aug. 18, 1978

[51] Int. Cl.$^2$ .............................................. C02C 1/14
[52] U.S. Cl. ........................................ 210/2; 210/12; 210/180; 210/188; 48/197 A; 71/10; 422/184; 422/193; 422/200; 119/28; 119/95
[58] Field of Search ........................ 48/197 A; 71/10; 422/184, 193, 200; 119/22, 28, 51 R, 95; 195/108, 127, 139; 210/2, 12, 18, 16, 71, 152, 175, 180, 188

[56] References Cited

U.S. PATENT DOCUMENTS

| 2,315,577 | 4/1943 | Bach | 210/12 |
| 3,156,646 | 10/1964 | Cameron | 210/16 |
| 3,865,695 | 2/1975 | Massier | 195/81 |
| 3,981,803 | 9/1976 | Coulthard | 210/180 |
| 4,008,689 | 2/1977 | Albers | 119/28 |
| 4,011,837 | 3/1977 | Ksioszk | 119/19 |
| 4,100,023 | 7/1978 | McDonald | 48/197 A |

FOREIGN PATENT DOCUMENTS

| 764701 | 8/1971 | Belgium | 210/180 |
| 1411659 | 10/1975 | United Kingdom | 210/12 |
| 1452781 | 10/1976 | United Kingdom | 210/16 |

OTHER PUBLICATIONS

Organic Gardening and Farming, vol. 6, Oct. 1959, p. 26, "For the Suburban Gardener."

Primary Examiner—Robert H. Spitzer
Assistant Examiner—Ernest G. Therkorn
Attorney, Agent, or Firm—Fulwider, Patton, Rieber, Lee, Utecht

[57] ABSTRACT

A waste treatment system and method for anaerobic fermentation of animal excreta. The system includes a collection gutter for containing the excreta until a predetermined portion becomes liquified. When the liquid excreta reaches a predetermined level it passes from the gutter into one end of an elongated, collapsed bag. The bag progressively fills, the liquid excreta being maintained at a temperature conducive to fermentation. After a predetermined degree of fermentation has been achieved, the liquid excreta is tapped off for use as fertilizer. Gases formed in the process are vented off and can be burned to provide heat for maintaining the liquid excreta at the desired fermentation temperature.

5 Claims, 3 Drawing Figures

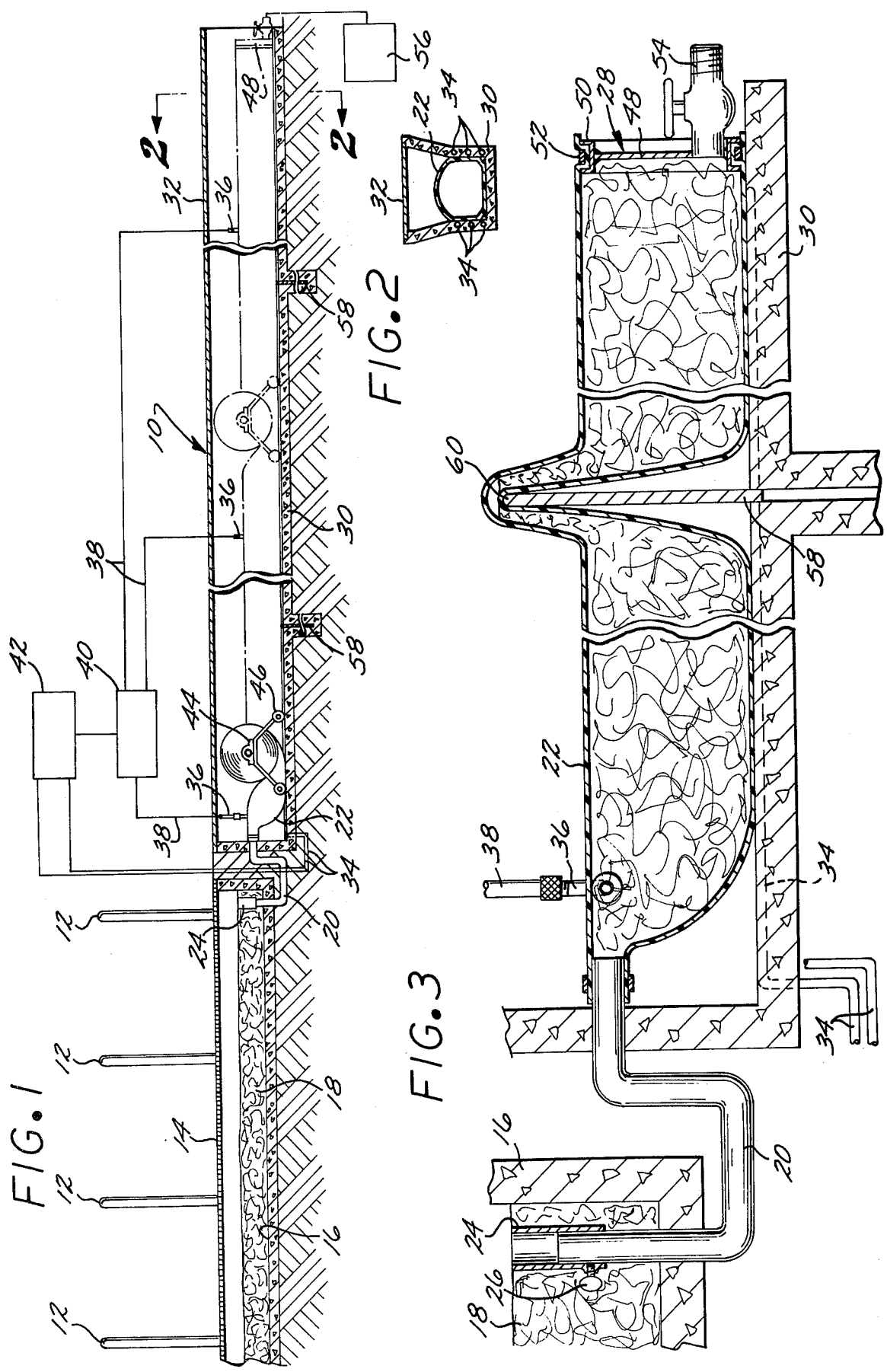
U.S. Patent    Sep. 25, 1979    4,169,048

ANAEROBIC FERMENTATION OF EXCRETA IN A COLLAPSIBLE BAG

CROSS-REFERENCE TO RELATED APPLICATION

The present invention is related to my U.S. Pat. No. 4,008,689, issued Feb. 22, 1977, and entitled "Waste Collection and Conversion System."

BACKGROUND OF THE INVENTION

1. Field of the Invention

The present invention relates to a waste treatment system and method and more particularly to a waste treatment system and method for anaerobic fermentation of animal excreta for conversion into combustible gases and fertilizer.

2. Description of the Prior Art

A large portion of underground water table pollution results from animal waste seepage, particularly in the warmer western and southern parts of the United States where there are larger concentrations of animals in small spaces, such as in dairy operations. Excreta from dairy cows is usually gathered in a relatively small area, and the liquid portion simply seeps down into the undergound water table.

Animal waste contains many elements which make it an ideal fertilizer, in addition to which the methane and other gases present are useful as a source of energy. However, prior art systems for converting the animal wastes to combustible gases and fertilizer have been ineffecient and uneconomical. For example, composting requires considerable labor and is not complete for approximately twelve months. Moreover, recovery of the methane gas produced during the composting process is dangerous because of the explosiveness of the gas in the presence of air.

My issued U.S. Pat. No. 4,008,689 discloses a reasonably effective system for converting animal excreta into useful combustible gases and fertilizer without polluting rivers and underground water. In that system the animal excreta is received in a trough and contained for a period of time sufficient to allow a predetermined portion of the excreta to become liquified. This is transferred to a fermentation tank, and the excreta is next pumped out after fermetation is completed. Although the system is a significant advance over the prior art, the air initially present in the fermentation tank present a potential danger of explosive combination with the methane generated in the process. The system was also characterized by significant items of cost, such as the tank and the means for withdrawing materials from the tank.

SUMMARY OF THE INVENTION

According to the present invention a waste treatment system and method is provided for anaerobic fermentation of animal excreta. The system includes a collection gutter for receiving and containing the excreta, and also includes a transfer means for transferring the liquid excreta from the gutter to an elongated collapsible bag. The transfer is through a liquid seal which prevents passage of air and other gases along with the excreta. The bag is received in an elongated receptacle located adjacent the collection gutter, and is made of flexible material connected at one end to the transfer means. Its possible end is adapted for attachment to a suitable discharge means for discharge of the excreta to a storage tank, tanker truck or the like.

The liquid excreta is received by the bag in its collapsed state so that relatively no air or other gas is present in the bag prior to receipt of the liquid excreta. In one embodiment the bag is wound upon a bag reel adapted to move down the length of the receptacle as the bag is filled, the incoming excreta being effective to progressively unroll the bag.

Suitable vent means are provided to carry off gases developed during the fermentation process. These gases can be burned to provide heat to maintain the liquid excreta at a temperature conductive to its fermentation.

The system includes movable barrier means for engaging the bag at one or more points between its opposite ends to obstruct the flow of liquid excreta. Consequently, the excreta flow can be halted adjacent the discharge end of the bag to enable attachment of the bag to the discharge means, or a plurality of such barrier means can be employed to isolate the excreta in various portions of the bag. The plurality of barrier means are operated to advance the excreta in batches down the length of the bag. The present system can thus be operated continuously, or in batch fashion.

The present invention and method is adapted to convert animal excreta into combustible gases and valuable fertilizer without any need for significant labor, in contrast to a composting operation, for example. The fermentation process takes place in the absence of air so that there is no opportunity for an explosive reaction to take place. Excess methane gas produced in the process can be used to operate much of the equipment used in the typical dairy.

The present waste treatment method takes approximately four to eight weeks, as compared to the twelve months required for composting, for example.

The liquid portion of animal excreta, which contains the highest concentration of available nitrogen, is prevented from draining into the soil and polluting the water table, and is instead completely collected for conversion into fertilizer and combustible gases.

Other objects and features of the invention will become apparent from consideration of the following description taken in connection with the accompanying drawings.

BRIEF DESCRIPTION OF THE DRAWINGS

FIG. 1 is a partially diagrammatic illustration in partial cross section of a waste treatment system according to the present invention;

FIG. 2 is a view taken along the line 2—2 of FIG. 1; and

FIG. 3 is an enlarged view of the fermentation bag and the associated receptacle, the bag and receptacle being foreshortened to conserve drawing space.

DESCRIPTION OF THE PREFERRED EMBODIMENT

Referring now to the drawings, there is illustrated a waste treatment system 10 for anaerobic fermentation of animal excreta according to the present invention.

In a typical dairy operation most dairy cow waste is collected and carried off by conveyors or heavy equipment and piled in a central collecting area or diluted in a collecting pond. Unfortunately the liquid constituent, which has the highest nitrogen content, drains away into the soil and pollutes the water table.

In the present system 10, the dairy cows are held in feeding position by a plurality of usual cattle stanchions 12. In this position the waste falls through a grating 14 and into an underlying elongated gutter 16. The gutter 16 is preferably made of, or used in conjunction with, thermal insulating material to maintain the excreta in the gutter 16 at a desired temperature of approximately 95° Fahrenheit. In one proposed embodiment the gutter 16 is made of relatively thick concrete having an exterior liner or blanket of polyurethane foam or the like. However, any suitable thermal insulating material known to those skilled in the art may be used.

The process of fermentation taking place in the gutter 16 is actually a continuation of the digestive process of the cow and the desired gutter temperature of 95° F. is an approximation of the cow's body temperature. The continuing addition of excreta by the cows amounts to about 100 pounds per cow per day, which tends to keep the fermentation temperature at somewhere close to the desired 95° F.

A sealed crust forms on the top of freshly deposited excreta 18, tending to keep gases in. In approximately 7 to 10 days the waste or excreta liquifies, breaking through the crust and rising in level. This liquid excreta overflows into the inlet end of the U-shaped transfer conduit 20 and passes into an elongated, collapsible fermentation bag 22.

The inlet end of the conduit 20 is vertically oriented and slidably mounts a vertically adjustable cylindrical sleeve 24. The sleeve 24 can be raised and lowered relative to the conduit 20 and tightened in position by a screw 26. The vertical height of the sleeve 24 controls the height to which the liquid excreta must rise before spilling into the conduit 20, and this spillage level is selected according to the rate at which the liquification of the excreta occurs and the volumes involved.

It is noted that once liquid excreta flows into the conduit 20, the conduit is always filled. This provides a liquid seal which desirably prevents entry of any air into the bag 22 through the conduit.

In one proposed embodiment the bag 22 is approximately 80 to 100 feet long and eight feet in diameter. Its inlet end is connected to the discharge end of the conduit 20 by any suitable means. The discharge end of the bag is also adapted to be connected to a suitable discharge means 28, as will subsequently be described.

The bag 22 is made of any suitable flexible material permitting it to be collapsed. Various materials for this material will suggest themselves to those skilled in the art. One suitable material is polyethylene, which it is anticipated will have an operating life of between six and eight months. The used bag is then discarded and a new bag is fitted into position.

The bag 22 is received within an elongated receptacle 30 dimensioned to receive it, as seen in FIGS. 2 and 3. The receptacle is located adjacent the gutter 16 and is made of or used with a similar thermal insulating material to maintain the excreta in the bag 22 at or near the desired fermentation process temperature of approximately 95° F. In colder weather a thermal blanket or cover 32 is preferably used to overlie the receptacle. During summer months the cover 32 may be removed to allow the sun to raise the heat of the bag contents to the desired temperature.

It may be necessary to supplement the available heat of the cow excreta, in which case a plurality of heating lines or tubes 34 can be located in or upon the walls of the gutter 16 and receptacle 30, as best seen in FIG. 2.

How water circulation then provides more precise control of the gutter and receptacle temperature. The water can be heated by the system which is diagrammatically illustrated in FIG. 1. This system includes a plurality of vents 36 extending laterally and thence upwardly of the bag through the cover 32. These lines are connected through gas lines 38 to a heater 40 which is operative to burn the gases and heat water circulated through the tubes 34 by a circulation system 42.

Various other ways of maintaining the desired gutter and receptacle temperatures can be used if desired, the system disclosed merely being exemplary.

The amounts of methane gas generated amount to as much as 27 cubic feet per cow per day, and the output of the heater 40 can therefore be used to provide for other energy needs of the typical dairy operation, as will be apparent.

Although the elongated bag 22 can be laid out full length in the receptacle 30 in a collapsed state, it is preferably rolled or wound upon a bag reel 44. The reel 44 is mounted upon a wheeled frame 46 which is adapted to roll upon the bottom of the receptacle 30 from one end to the other. In starting up the present waste treatment system and method, the bag reel 44 is preferably rolled to the inlet end of the receptacle 30. The inlet end of the bag 22 is connected to the discharge end of the transfer conduit 20 to receive liquified excreta. As the excreta flows through the conduit 20 the bag 22 fills and swells as the fermentation process continues.

During progressive filling of the bag, the force of the incoming excreta causes the reel 44 to roll toward the discharge end of the receptacle 30. This causes the bag 22 to unwind. The vents 36 can be manually connected to the gas lines 38 as they become aligned, but preferably the gas lines are made of flexible tubing and are initially connected to the vents 36 before the bag is unwound. In the latter case the gas lines move with the unrolling bag 22 and are trained through the cover 32 in such a way that the vents 36 and lines 38 do not interfere with unrolling of the bag.

It is important to note that there is no significant air in the initially collapsed bag 22. Consequently, there is no possibility for an explosive mixture of methane and air to occur.

When the reel 44 nears the discharge end of the receptacle 30, the discharge end of the bag 22 must be attached to the discharge means 28. Although means can be envisioned for having a connection between the discharge end of the bag and the discharge means at all times, the arrangement tends to be somewhat complex. That is, the connection must allow unrestricted unrolling of the bag. Consequently, for simplicity it is preferred to manually attach the bag discharge end about a circular end wall 48. The wall 48 includes an annular, channel-shaped edge 50 adapted to receive a ring clamp 52 to clamp the material of the bag 22 against the edge 50. The wall 48 mounts a discharge valve 54 adapted for connection to a tanker truck (not shown) or, as illustrated, to a storage tank 56. The tank 56 is indicated diagrammatically in FIG. 1 and preferably incorporates a level sensing and pump mechanism (not shown) adapted to pump the tank contents down to a predetermined level, the discharged material being automatically emptied into containers or the like for transport.

The substantially completely digested or fermented liquid excreta discharged from the valve 54 contains high levels of nitrogen and is extremely useful as a fertilizer.

One or more barrier means 58 are preferably employed to control the flow of liquid excreta through the bag 22, as may be necessitated by the rate of fermentation. Although the barrier means may take any form effective to obstruct liquid flow, one suitable means 58 includes a transverse wall 60 vertically movable by hydraulic rams or the like (not shown) from a recessed position below the floor of the receptacle 30 to the raised position illustrated in FIG. 3. Preferably the present apparatus is allowed to operate substantially continuously and without attention except when the bag is nearly completely unrolled. However, should fermentation not be occurring as rapidly as desired, the movable walls 60 can be employed to advance batches of liquid excreta only when it is determined that the degree of fermentation is acceptable. Also, operation of one of the barrier means adjacent the discharge end of the bag 22 is also helpful in preventing flow during attachment of the discharge end of the bag 22 to the end wall 48.

In the preferred continuous operation of the present system and method there is usually no need for more than one person to monitor the general operation and attend to transporting away the discharge product of the fermentation process for use as fertilizer.

The fertilizer product of the present invention is uniquely suited for use in hydroponic gardening. Heretofore, cow excreta, for example, was generally unsuitable for hydroponic gardening. However, fermentation of cow excreta is sufficiently advanced in the present method that it can be safely and effectively used in hydroponic gardening.

In hydroponic gardening the plants' roots absorb mineral salts in combination with water through the process of osmosis. Such salts preferably include nitrogen, phosphorus, potassium, calcium, magnesium, sulphur, iron, manganese, boron, zinc and copper, all of which are not only found in significant quantities in the liquid fertilizer product of the present invention, but also in a form in which they are immediately available as nutrients for plant life.

Various modifications and changes may be made with regard to the foregoing detailed description without departing from the spirit of the invention.

I claim:

1. A waste treatment method for anaerobic fermentation of animal excreta comprising the steps of:
    receiving excreta in an open gutter;
    containing the excreta in the gutter until a predetermined portion of the excreta becomes liquified;
    draining off liquid excreta when it reaches a predetermined level in the gutter;
    receiving the drained off liquid excreta in one end of an elongated, collapsed bag devoid of any significant quantity of air;
    applying a barrier means to the bag adjacent said one end to prevent liquid excreta from flowing into the remainder of the bag;
    moving the barrier means along the length of the bag to allow the bag to become progressively filled with liquid excreta;
    maintaining the liquid excreta in the bag at a temperature conducive to fermentation of the liquid excreta;
    venting gases from the bag; and
    tapping off liquid excreta from the opposite end of the bag after a predetermined degree of fermentation has been achieved.

2. In a waste treatment system for anaerobic fermentation of animal excreta, including a collection gutter for receiving and containing such excreta, and transfer means for transferring liquid excreta from said gutter, said transfer means having a portion preventing passage of air and other gases therethrough when such portion is filled with such liquid excreta, an improved fermentation apparatus comprising:
    an elongated receptacle located adjacent the collection gutter;
    an elongated bag in said receptacle connected at one end to said transfer means for receiving liquid excreta, and adapted for connection at its opposite end to discharge means, said bag being made of flexible material whereby it may be collapsed prior to receipt of liquid excreta thereby to substantially remove air and other gases from the interior of said bag prior to receipt of the liquid excreta; and
    barrier means operative to press said bag closed adjacent said one end to prevent flow of liquid excreta therepast, said barrier means being adapted for movement along the length of said receptacle to enable said bag to be progressively opened farther along its length for filling said bag filled with liquid excreta.

3. A waste treatment system according to claim 1 wherein said barrier means comprises a bag reel upon which said bag can be wound, said bag reel being adapted for movement along the length of said receptacle for unwinding said bag as said bag fills with liquid excreta.

4. A waste treatment system according to claim 1 and including thermal insulation means adjacent at least the sides and bottom of said receptacle for maintaining liquid excreta in said bag at a desired temperature level.

5. In a waste treatment system for anaerobic fermentation of animal excreta, including a collection gutter for receiving and containing such excreta, and transfer means for transferring liquid excreta from said gutter, said transfer means having a portion preventing passage of air and other gases therethrough when such portion is filled with such liquid excreta, an improved fermentation apparatus comprising:
    an elongated receptacle located adjacent the collection gutter;
    an elongated bag in said receptacle connected at one end to said transfer means for receiving liquid excreta, and adapted for connection at its opposite end to discharge means, said bag being made of flexible material whereby it may be collapsed prior to receipt of liquid excreta thereby to substantially remove air and other gases from the interior of said bag prior to receipt of the liquid excreta; and
    a plurality of barrier means located externally of said bag and longitudinally spaced apart along the length of said receptacle, each of said barrier means being separately operable between a projected position, to engage and squeeze said bag closed to prevent passage of liquid excreta, and a retracted position out of engagement with said bag to open said bag and allow passage of liquid excreta.

* * * * *